(12) United States Patent
Kim et al.

(10) Patent No.: US 12,023,317 B2
(45) Date of Patent: Jul. 2, 2024

(54) COMPOSITION FOR AMELIORATING PSORIASIS COMPRISING CIMICIFUGOLIDE A AS ACTIVE INGREDIENT

(71) Applicant: KOREA INSTITUTE OF SCIENCE AND TECHNOLOGY, Seoul (KR)

(72) Inventors: Jin Chul Kim, Gangneung-si (KR); Jung Yeob Ham, Gangneung-si (KR); Tae Jung Kim, Gangneung-si (KR); Dorjsembe Banzragch, Gangneung-si (KR); Ha Neul Ju, Gangneung-si (KR); Hyung Seok Yu, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 8 days.

(21) Appl. No.: 17/687,682

(22) Filed: Mar. 7, 2022

(65) Prior Publication Data

US 2023/0087636 A1    Mar. 23, 2023

(30) Foreign Application Priority Data

Sep. 17, 2021   (KR) ........................ 10-2021-0124652

(51) Int. Cl.

| | | |
|---|---|---|
| A61K 31/365 | (2006.01) |
| A61K 9/00 | (2006.01) |
| A61K 9/16 | (2006.01) |
| A61K 9/20 | (2006.01) |
| A61K 31/07 | (2006.01) |
| A61K 31/197 | (2006.01) |
| A61K 31/355 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/519 | (2006.01) |
| A61K 31/525 | (2006.01) |
| A61K 31/714 | (2006.01) |
| A61K 33/00 | (2006.01) |
| A61K 33/06 | (2006.01) |
| A61K 33/10 | (2006.01) |
| A61K 33/26 | (2006.01) |
| A61K 33/30 | (2006.01) |
| A61K 33/42 | (2006.01) |
| A61K 36/73 | (2006.01) |
| A61K 47/12 | (2006.01) |
| A61K 47/20 | (2006.01) |
| A61P 37/06 | (2006.01) |

(52) U.S. Cl.
CPC .......... *A61K 31/365* (2013.01); *A61K 9/0019* (2013.01); *A61K 9/0056* (2013.01); *A61K 9/0095* (2013.01); *A61K 9/1623* (2013.01); *A61K 9/2013* (2013.01); *A61K 9/2018* (2013.01); *A61K 9/205* (2013.01); *A61K 9/2059* (2013.01); *A61K 31/07* (2013.01); *A61K 31/197* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/714* (2013.01); *A61K 33/00* (2013.01); *A61K 33/06* (2013.01); *A61K 33/10* (2013.01); *A61K 33/26* (2013.01); *A61K 33/30* (2013.01); *A61K 33/42* (2013.01); *A61K 36/73* (2013.01); *A61K 47/12* (2013.01); *A61K 47/20* (2013.01); *A61P 37/06* (2018.01); *A61K 2236/331* (2013.01); *A61K 2236/333* (2013.01)

(58) Field of Classification Search
CPC .............................. A61K 31/365; A61P 37/06
See application file for complete search history.

(56) References Cited

FOREIGN PATENT DOCUMENTS

| | | |
|---|---|---|
| CN | 101618106 A | 1/2010 |
| KR | 10-2000-0064607 A | 11/2000 |
| KR | 10-2012-0077808 A | 7/2012 |
| KR | 10-2018-0053292 A | 5/2018 |
| KR | 10-1869353 B1 | 6/2018 |
| KR | 10-2018-0134856 A | 12/2018 |

OTHER PUBLICATIONS

Ma et al. Planta Med., 2013, vol. 79, pp. 308-311 (Year: 2013).*
Granica et al. Food Chemistry, 2017, vol. 221, pp. 1851-1859 (Year: 2017).*
Korean Office Action dated Jan. 2, 2024, issued in corresponding KR 10-2021-0124652, 5 pp.
Machine English Translation of Korean Office Action dated Jan. 2, 2024, issued in corresponding KR 10-2021-0124652, 5 pp.
Qin Zhang, et al., Korean J Plant DNA Damage Protection and Anti-inflammatory Activity of Different Solvent Fractions from Aruncus dioicus var. kamtschaticus, Res. 2014. vol. 27, No. 6, pp. 714-719, (2014).

* cited by examiner

*Primary Examiner* — James D. Anderson
(74) *Attorney, Agent, or Firm* — CANTOR COLBURN LLP

(57) ABSTRACT

Disclosed is a composition for use in preventing, alleviating, or treating psoriasis containing cimicifugolide A as an active ingredient.

5 Claims, 13 Drawing Sheets

COMPOSITION FOR AMELIORATING PSORIASIS COMPRISING CIMICIFUGOLIDE A AS ACTIVE INGREDIENT

CROSS-REFERENCE TO RELATED APPLICATION

This application claims under 35 U.S.C. § 119(a) the benefit of priority from Korean Patent Application No. 10-2021-0124652, filed on Sep. 17, 2021, the entire contents of which are incorporated herein by reference.

BACKGROUND

(a) Technical Field

The present disclosure relates to a composition for ameliorating, preventing, or treating an autoimmune skin disease, particularly psoriasis, containing cimicifugolide A as an active ingredient.

(b) Background Art

Psoriasis is a common autoimmune skin disease that shows papules with silvery white scales, and presents a wide variety of symptoms, including generalized exfoliative dermatitis, erythema, pruritus, dryness, and burning, which vary in distribution and severity from person to person. Although psoriasis occurs worldwide, there is a marked difference in the frequency of incidence between races and ethnicities, and the clinical course may vary, but it generally follows a cyclical pattern with repeated improvement and deterioration. Although the pathogenesis of psoriasis has not yet been fully elucidated, recently reported research results suggest that inflammation plays an important role, such as infiltration of inflammatory cells, increase in immune activation molecules, Th1 and Th17 responses, abnormal changes in inflammation-related cytokines, and the like.

Since psoriasis is a chronic recurrent disease, it is necessary to apply a therapeutic method that shows excellent effects and has fewer side effects. Known therapies include local treatment, systemic treatment, phototherapy, and treatment using biological products. In mild cases, local treatment is generally performed, and in severe cases, UV therapy or systemic treatment is principally performed.

However, there are not many known functional formulations used for the treatment of psoriasis.

CITATION LIST

Patent Literature (Patent Document 1) Korean Patent Application Publication No. 10-2000-0064607
(Patent Document 2) Korean Patent Application Publication No. 10-2018-0134856
(Patent Document 3) Korean Patent Application Publication No. 10-2018-0053292

SUMMARY OF THE DISCLOSURE

With the goal of solving the above problems, the present inventors have searched for compositions for preventing and treating psoriasis, and ascertained the possibility of alleviating psoriasis through phototherapy using natural products based on increased moisture content, decreased moisture loss, and inhibition of skin morphological changes and inflammation expression when cimicifugolide A is administered, thus culminating in the present invention.

Accordingly, the present invention is intended to provide a pharmaceutical composition for ameliorating, preventing, or treating an autoimmune skin disease containing cimicifugolide A as an active ingredient, a kit including the pharmaceutical composition, and a method of ameliorating or treating an autoimmune skin disease, particularly psoriasis, including administering the pharmaceutical composition.

The objects of the present invention are not limited to the foregoing. The objects of the present invention will be able to be clearly understood through the following description and to be realized by the means described in the claims and combinations thereof.

In order to accomplish the above object, the present invention provides the following composition.

An aspect of the present invention provides a composition for ameliorating, preventing, or treating an autoimmune skin disease containing cimicifugolide A of Chemical Formula 1 below as an active ingredient.

[Chemical Formula 1]

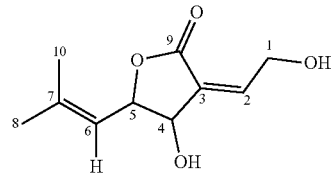

In the composition for ameliorating, preventing, or treating an autoimmune skin disease according to an aspect of the present invention, cimicifugolide A may be isolated from *Aruncus dioicus* var. *kamtschaticus*.

In the composition for ameliorating, preventing, or treating an autoimmune skin disease according to an aspect of the present invention, cimicifugolide A may be isolated from an extract of *Aruncus dioicus* var. *kamtschaticus* using water, a $C_1$-$C_6$ alcohol, or a $C_1$-$C_6$ alcohol aqueous solution.

In the composition for ameliorating, preventing, or treating an autoimmune skin disease according to an aspect of the present invention, cimicifugolide A may be isolated from an ethyl acetate fraction of an *Aruncus dioicus* var. *kamtschaticus* extract.

In the composition for ameliorating, preventing, or treating an autoimmune skin disease according to an aspect of the present invention, the autoimmune skin disease may be psoriasis.

The composition for ameliorating, preventing, or treating an autoimmune skin disease according to an aspect of the present invention may prevent, ameliorate, or treat psoriasis by decreasing skin moisture loss due to psoriasis, increasing skin moisture content, reducing a change in skin thickness due to psoriasis, or decreasing an area of skin flare due to psoriasis.

In an embodiment of the present invention, the composition may prevent, ameliorate, or treat psoriasis by reducing the level of at least one inflammatory cytokine selected from among IL-1β, CCL5, CCL20, CXCL8, S100A8, and S100A9.

The composition according to an aspect of the present invention may be a functional health food.

The composition according to an aspect of the present invention may be a pharmaceutical composition.

The composition according to an aspect of the present invention may be a functional cosmetic composition.

BRIEF DESCRIPTION OF THE DRAWINGS

The above and other features of the present invention will now be described in detail with reference to certain exemplary embodiments thereof illustrated in the accompanying drawings, which are given hereinbelow by way of illustration only, and thus are not limitative of the present invention, and wherein.

DETAILED DESCRIPTION

Figure 1:
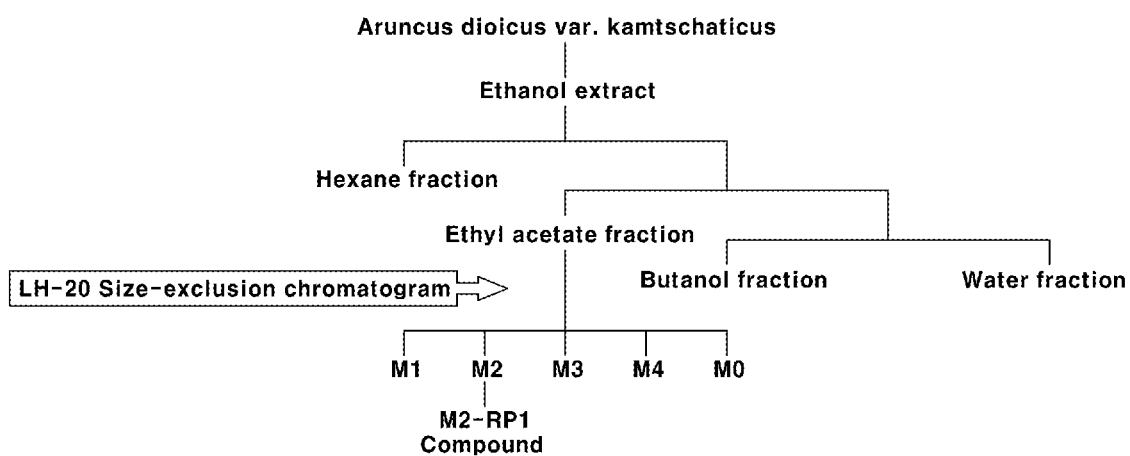
FIG. 1 schematically shows a process of separating compound M2-RP1 of Example 1-3 according to the present invention.

Unless otherwise specified, all numbers, values, and/or representations that express the amounts of ingredients, reaction conditions, and compositions used herein are to be taken as approximations including various uncertainties affecting measurement that inherently occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

Hereinafter, a detailed description will be given of the present invention.

An aspect of the present invention pertains to a composition for ameliorating, preventing, or treating an autoimmune skin disease containing cimicifugolide A of Chemical Formula 1 below as an active ingredient:

[Chemical Formula 1]

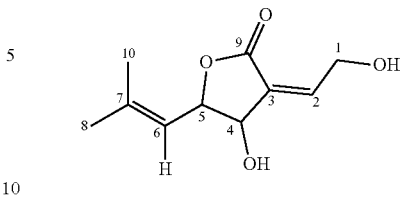

In the present invention, cimicifugolide A is described by the formula (Z)-4-Hydroxy-3-(2-hydroxyethylidene)-5-(2-methylprop-1-en-1-yl)dihydrofuran-2(3H)-one and has a molecular weight of 198.22.

Cimicifugolide A according to the present invention may be prepared through any method, and it is possible to prepare the same through organic synthesis or by separating a target component from a natural product. In one embodiment, cimicifugolide A may be provided by being separated from natural products.

In the composition for ameliorating, preventing, or treating an autoimmune skin disease according to an aspect of the present invention, cimicifugolide A is isolated from *Aruncus dioicus* var. *kamtschaticus*.

As used herein, the term "*Aruncus dioicus* var. *kamtschaticus*" is a perennial herb that grows in alpine areas, and grows wild in semi-shaded or shaded areas full of leaf litter. The plant is 30 to 100 cm tall, and the leaves are 3 to 10 cm long and 1 to 6 cm wide and have long glossy petioles. These leaves are pinnate compound leaves that are split about 2-3 times, like pinnae of a bird's feather, and have a sharp tip and toothed margins. The flowers are white, 10 to 30 cm long, spread out in a fan-like pattern, and bloom from the bottom and rise upwards. The fruits ripen in July and August, are brown, oval, and about 0.3 cm long, and are shiny when ripe. In the present invention, young leaves of *Aruncus dioicus* var. *kamtschaticus* were used.

*Aruncus dioicus* var. *kamtschaticus* as used in the present invention may also be known as goat's beard.

In the composition for ameliorating, preventing, or treating an autoimmune skin disease according to an aspect of the present invention, cimicifugolide A is isolated from the extract of *Aruncus dioicus* var. *kamtschaticus* using water, a $C_1$-$C_6$ alcohol, or a $C_1$-$C_6$ alcohol aqueous solution.

In the composition according to an aspect of the present invention, cimicifugolide A is isolated from the ethyl acetate fraction of the *Aruncus dioicus* var. *kamtschaticus* extract.

The *Aruncus dioicus* var. *kamtschaticus* extract may be extracted from various organs of natural, hybrid, and variegated plants, for example, from the roots, stems, leaves, flowers, fruit meat, and fruit skins, as well as from plant tissue cultures and stem roots. The *Aruncus dioicus* var. *kamtschaticus* extract of the present invention may be a solvent extract extracted using an extraction solvent, a fraction obtained by adding a fractionation solvent to the extract prepared through extraction using the extraction solvent, or a purified product obtained from the fraction through chromatography. The extraction solvent may be water, an organic solvent, or a mixture thereof, which may be used for extraction of natural products. The extraction solvent may be water, a $C_1$-$C_6$ alcohol, or a mixture thereof, for example water or ethanol. The *Aruncus dioicus* var. *kamtschaticus* extract of the present invention may be prepared according to a typical method of preparing a plant extract. More specifically, the *Aruncus dioicus* var. *kamtschaticus* extract may be prepared in a manner in which the dried product of the stem root of *Aruncus dioicus* var. *kamtschaticus* from which impurities have been removed is pulverized, added with an extraction solvent, and extracted. The extraction method using the solvent may be a cold extraction method, a hot extraction method, a solubilization extraction method, a reflux extraction method, or a sonication extraction method.

As used herein, the term "fraction" refers to a result obtained by performing fractionation in order to separate a specific component or a group of specific components from a mixture including various components.

Moreover, the fraction of the extract may be prepared in a manner in which the extract prepared through the extraction method is added with a fractionation solvent and then a fraction is obtained based on the polarity of the fractionation solvent. The method of obtaining the fraction may be performed through a fractionation method or a separation method using layer separation. More specifically, after adding the fractionation solvent to the extract, for example, after sequentially adding ethyl acetate and water as fractionation solvents, layer-separated ethyl acetate and water fractions may be obtained. The fractionation method using layer separation may be conducted in a manner in which the solvents are sequentially added to the extract depending on the extent of nonpolarity thereof, and a fraction is obtained through layer separation for each application. For example, ethyl acetate is added to the ethanol aqueous solution extract and the layer-separated ethyl acetate layer is fractionated to obtain an ethyl acetate fraction, after which a water fraction, which is a layer remaining after separating the ethyl acetate fraction, may be obtained. Chromatography for purification of the fraction may be performed using any of various chromatographic methods such as silica gel column chromatography, thin-layer chromatography (TLC), high-performance liquid chromatography (HPLC), etc.

In the composition according to an aspect of the present invention, the concentration of the $C_1$-$C_6$ alcohol aqueous solution is 10% to 90% (v/v).

In the composition according to an aspect of the present invention, the *Aruncus dioicus* var. *kamtschaticus* extract is an extract of the shoot or root zone of *Aruncus dioicus* var. *kamtschaticus*, and the *Aruncus dioicus* var. *kamtschaticus* extract is an ethanol extract.

The $C_1$-$C_6$ alcohol may be methanol, ethanol, propanol, butanol, pentanol, or hexanol. Also, the $C_1$-$C_6$ alcohol aqueous solution may have a concentration of 5 to 99%. In a preferred embodiment, the extraction solvent is ethanol.

In the composition according to an aspect of the present invention, the *Aruncus dioicus* var. *kamtschaticus* fraction is an ethyl acetate or water fraction of the *Aruncus dioicus* var. *kamtschaticus* extract.

In the composition for ameliorating, preventing, or treating an autoimmune skin disease according to an aspect of the present invention, the autoimmune skin disease is psoriasis, lupus, or atopic dermatitis.

In the composition according to an aspect of the present invention, the autoimmune skin disease is psoriasis.

Here, psoriasis shows symptoms such as generalized exfoliative dermatitis, erythema, pruritus, dryness, burning, and the like.

The composition for ameliorating, preventing, or treating an autoimmune skin disease according to an aspect of the present invention is capable of ameliorating or treating psoriasis by decreasing skin moisture loss due to psoriasis, increasing skin moisture content, alleviating changes in skin thickness due to psoriasis, or decreasing the area of skin flare due to psoriasis.

The composition for ameliorating, preventing, or treating an autoimmune skin disease according to aspect of the present invention prevents, ameliorates, or treats psoriasis by reducing the level of at least one inflammatory cytokine selected from among IL-1β, CCL5, CCL20, CXCL8, S100A8, and S100A9.

In one embodiment, the pharmaceutical composition of the present invention is able to increase skin moisture content or to inhibit changes in the thickness of the ear and skin epithelium and expression of inflammation. For changes in skin morphology, the thickness of the surface of the ear and skin becomes greater than that of a normal control group due to the inflammatory response, and the expression of inflammation is caused by increasing the number of inflammatory cells and T cells due to the inflammatory response, which may be inhibited and ameliorated using the composition of the present invention. In one embodiment of the present invention, it has been confirmed that the use of the *Aruncus dioicus* var. *kamtschaticus* extract or the fraction thereof is capable of reducing the size of the damaged area and simultaneously significantly increasing skin moisture content and decreasing moisture loss in the fraction-treated group compared to the psoriasis-induced group after termination of the experiment. Moreover, it has been confirmed that the expression of inflammation is reduced at the protein and RNA levels.

The composition according to an aspect of the present invention is a pharmaceutical composition.

Carriers, excipients, and diluents that may be contained in the pharmaceutical composition of the present invention include at least one selected from among lactose, dextrose, sucrose, sorbitol, mannitol, xylitol, erythritol, maltitol, starch, acacia gum, alginate, gelatin, calcium phosphate, calcium silicate, cellulose, methyl cellulose, hydroxymethyl cellulose, microcrystalline cellulose, silicified microcrystalline cellulose, povidone, crospovidone, croscarmellose sodium, polyvinylpyrrolidone, water, methylhydroxybenzoate, propylhydroxybenzoate, Noisirin, colloidal silicon dioxide, talc, magnesium stearate, colloidal magnesium stearate, and mineral oil.

The dose of the pharmaceutical composition of the present invention may be determined by those skilled in the art in consideration of well-known factors in the medical field, such as the purpose of use, severity of disease, age, body weight, health status, gender, drug sensitivity, administration time or route, and the type of material used as an active ingredient. The composition may include an *Aruncus dioicus* var. *kamtschaticus* extract or a fraction thereof alone as a single active ingredient. Specifically, the composition may not include any active ingredient other than the *Aruncus dioicus* var. *kamtschaticus* extract or the fraction thereof. In one embodiment, a method of treating psoriasis in a subject is provided, the method including administering the pharmaceutical composition described above to a subject in an amount effective for the prevention or treatment of psoriasis. Here, the subject may be a mammal. The mammal may be a human, dog, cat, cow, goat, or pig. That is, the subject may be a human or non-human animal, and may be a human or a non-human mammal. Administration may be performed through any general route, so long as it is able to reach the target tissue. For example, skin application, intraperitoneal administration, intravenous administration, intramuscular administration, subcutaneous administration, intradermal administration, transdermal patch, oral administration, intranasal administration, intrapulmonary administration, intrarectal administration, etc. may be carried out, and particularly, a skin application route or the like may be used.

Preferably, a skin application route is carried out. The preferred dose of the pharmaceutical composition of the present invention varies depending on the patient's age, body weight, and severity of disease, as well as the drug form and administration route and period, but may be appropriately selected by those skilled in the art. However, for a desirable effect, the pharmaceutical composition of the present invention may be administered at a daily dose of 0.001 mg/kg to 1 mg/kg, and preferably 0.1 mg/kg to 10 mg/kg. Administration may be carried out several times a day, preferably 1 to 6 times a day, at regular time intervals according to the judgment of a doctor or pharmacist.

Another aspect of the present invention pertains to a kit including the pharmaceutical composition according to an aspect of the present invention.

Still another aspect of the present invention pertains to a method of ameliorating or treating an autoimmune skin disease in a subject having an autoimmune skin disease, the method including administering the pharmaceutical composition according to an aspect of the present invention through a skin application route.

In the method of ameliorating or treating an autoimmune skin disease according to still another aspect of the present invention, the subject is an animal other than a human.

In the method of ameliorating or treating an autoimmune skin disease according to still another aspect of the present invention, the autoimmune skin disease is psoriasis.

The composition according to an aspect of the present invention is a functional health food.

The health food composition of the present invention includes an *Aruncus dioicus* var. *kamtschaticus* extract or a solvent fraction fractionated therefrom, but the type thereof is not particularly limited. Examples of the food may include drinks, meat, sausage, bread, biscuits, rice cakes, mixed grain powder, chocolate, candy, snacks, confectioneries, pizza, ramen, other noodles, gum, dairy products including ice cream, various soups, beverages, alcoholic beverages, vitamin complexes, milk products, and processed milk products. In addition thereto, food includes all functional health foods in the ordinary sense. In the present invention, the *Aruncus dioicus* var. *kamtschaticus* extract or the solvent fraction fractionated therefrom as an active ingredient may be added to food as it is or in combination with other foods or food ingredients, and may be appropriately used according to a typical method. The effective amount thereof may be appropriately determined depending on the purpose of use (for prevention or amelioration), and may fall in the range of 0.001 to 70 wt % based on the total weight of the health food. However, for long-term intake for health and hygiene or health control, the amount thereof may be equal to or less than the lower limit of the above range, and as long as there is no problem in terms of safety, the active ingredient may be used in an amount equal to or greater than the upper limit of the above range. For example, when manufacturing a health beverage, natural carbohydrates or flavoring agents may be included as additives that are commonly used in beverage manufacture, in addition to the active ingredient. The natural carbohydrates may include typical sugars such as monosaccharides (e.g. glucose, fructose, etc.), disaccharides (e.g. maltose, sucrose, etc.) and polysaccharides (e.g. dextrin, cyclodextrin, etc.), and sugar alcohols such as xylitol, sorbitol, erythritol, and the like. The natural carbohydrate may be contained in an amount of 1 to 20 wt %, preferably 5 to 10 wt %, based on the total weight of the health food. The flavoring agent may include natural flavoring agents (thaumatin, stevia extract, rebaudioside A, glycyrrhizin, etc.) and synthetic flavoring agents (saccharin, aspartame, etc.). In addition thereto, various nutrients, vitamins, minerals (electrolytes), flavors (synthetic or natural flavors), coloring agents, pectic acid and salts thereof, alginic acid and salts thereof, organic acids, protective colloidal thickeners, pH adjusters, stabilizers, preservatives, glycerin, alcohols, carbonation agents used in carbonated beverages, and the like may be contained. Moreover, natural fruit juice and pulp for the preparation of fruit juice beverages and vegetable beverages may be contained. Although there is no particular limitation on the amounts of these additives, such additives may be included in an amount of 0.1 to 20 wt % based on the total weight of the health food.

The composition according to an aspect of the present invention is a functional cosmetic composition. The composition according to an aspect of the present invention may be formulated in any one form selected from among a powder, granule, tablet, capsule, suspension, emulsion, syrup, aerosol, and external preparation. Here, the composition may be a cosmetic composition. The cosmetic composition of the present specification may be prepared in any formulation that is typical in the art, for example, a solution, suspension, emulsion, paste, gel, cream, lotion, powder, soap, surfactant-containing cleanser, oil, powder foundation, emulsion foundation, wax foundation, spray, etc., but is not limited thereto.

A better understanding of the present invention may be obtained through the following examples. However, these examples are merely set forth to illustrate the present invention, and are not to be construed as limiting the scope of the present invention.

Example 1: Preparation of Cimicifugolide A

In this Example, cimicifugolide A was prepared using *Aruncus dioicus* var. *kamtschaticus*. Here, the *Aruncus dioicus* var. *kamtschaticus* that was used was purchased from Sanyakcho Story located in Hongcheon-gun, Gangwon-do, Korea.

1-1: Preparation of Ethanol Extract 0.6 kg of young leaves of *Aruncus dioicus* var. *kamtschaticus* were immersed in 1.6 L of ethanol and allowed to stand at room temperature for 48 hours, which was repeated three times. The resulting solution was filtered through filter paper to obtain a filtrate, which was then distilled under reduced pressure, thereby yielding 30 g of an extract.

2.89 kg of young leaves of *Aruncus dioicus* var. *kamtschaticus* were immersed in 8 L of ethanol, sonicated for 30 minutes, and allowed to stand at room temperature for 72 hours, which was repeated three times. The resulting solution was filtered through filter paper to obtain a filtrate, which was then distilled under reduced pressure, thereby yielding 30 g of an extract.

1-2. Preparation of Fraction

Ethyl Acetate Layer Fraction 30 g of the crude extract obtained in 1-1 above was dissolved in 200 mL of water, mixed with 200 mL of ethyl acetate, and allowed to stand at room temperature for 24 hours, followed by separation of the ethyl acetate layer. These procedures were performed three times to obtain an ethyl acetate layer, which was then concentrated under reduced pressure, thereby yielding 3 g of an ethyl acetate layer extract (hereinafter, referred to as an 'ethyl acetate fraction').

1-3. Separation of Ethyl Acetate Fraction Component

For additional component analysis of the fraction obtained in 1-2 above, fractions were obtained through LH-20 size-exclusion chromatography, followed by component analysis.

The component analysis process is schematically shown in FIG. 1.

Figure 2A:
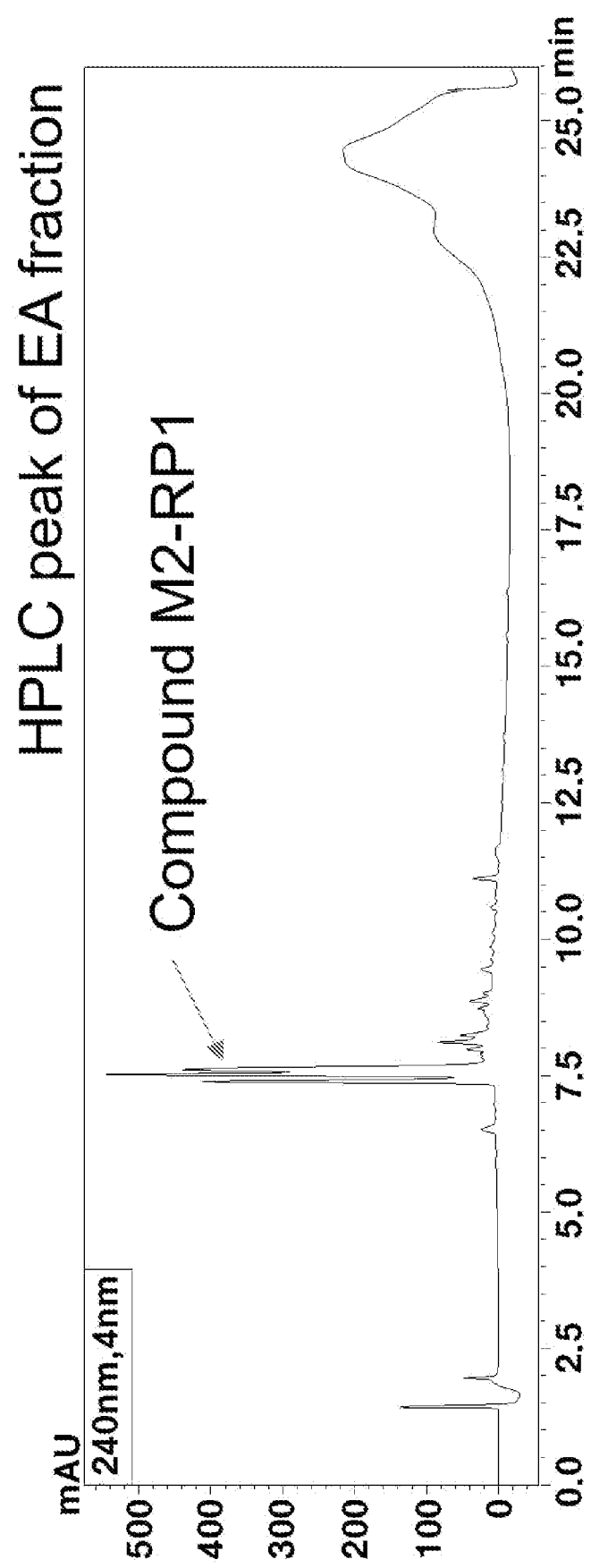
FIG. 2A to 2C show the results of separation of compound M2-RP1 in Example 1-3 according to the present invention.
Figure 2B:
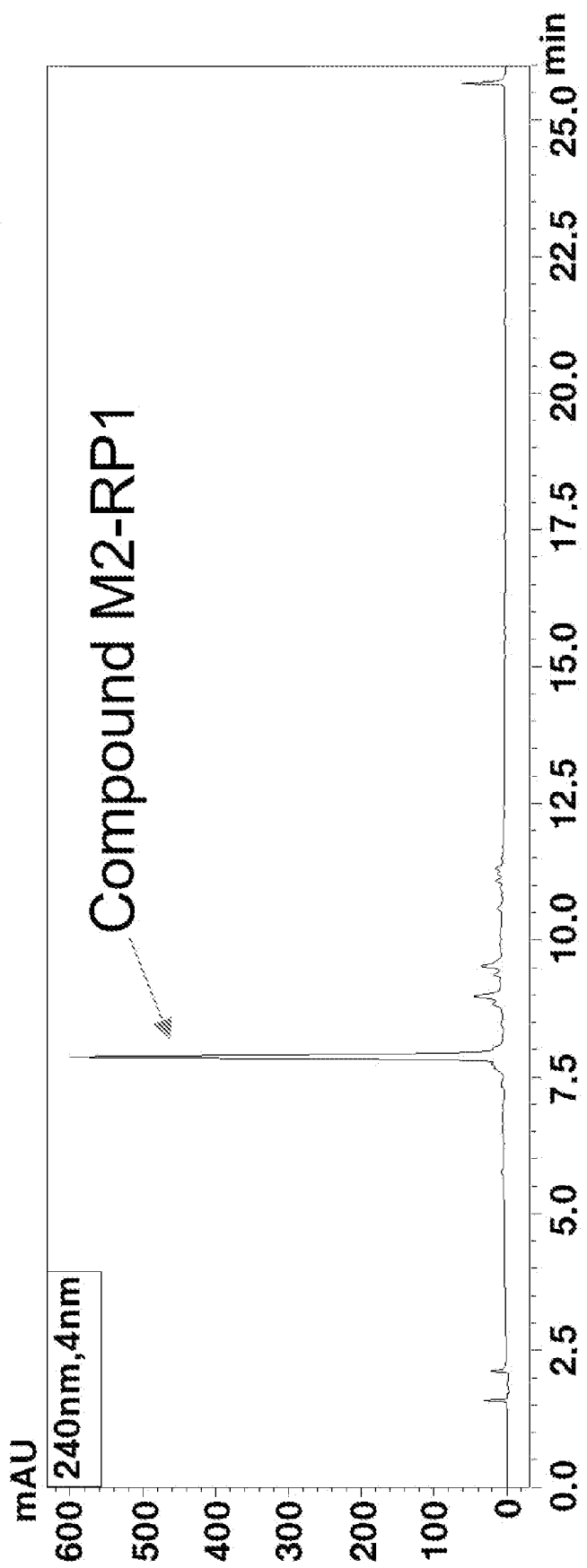
Figure 2C:
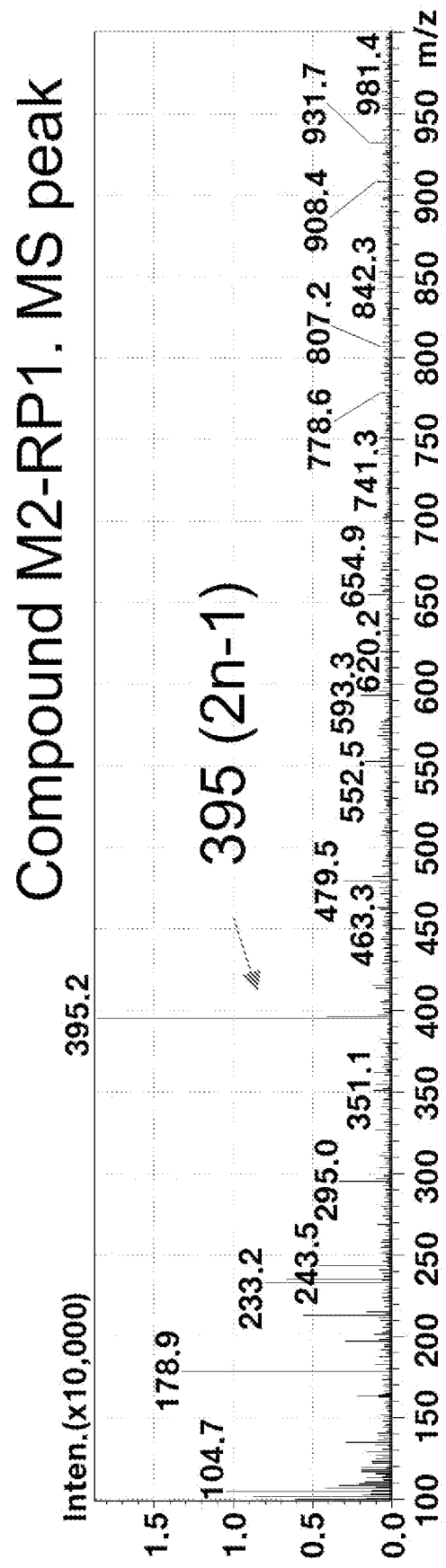

Among the analyzed components, a component named compound M2-RP1 was detected, and is schematically shown in FIG. 2A to 2C.

1-4. Identification of Compound M2-RP1

H NMR and carbon NMR were performed in order to identify the compound M2-RP1 component among the separated components.

Figure 3A:
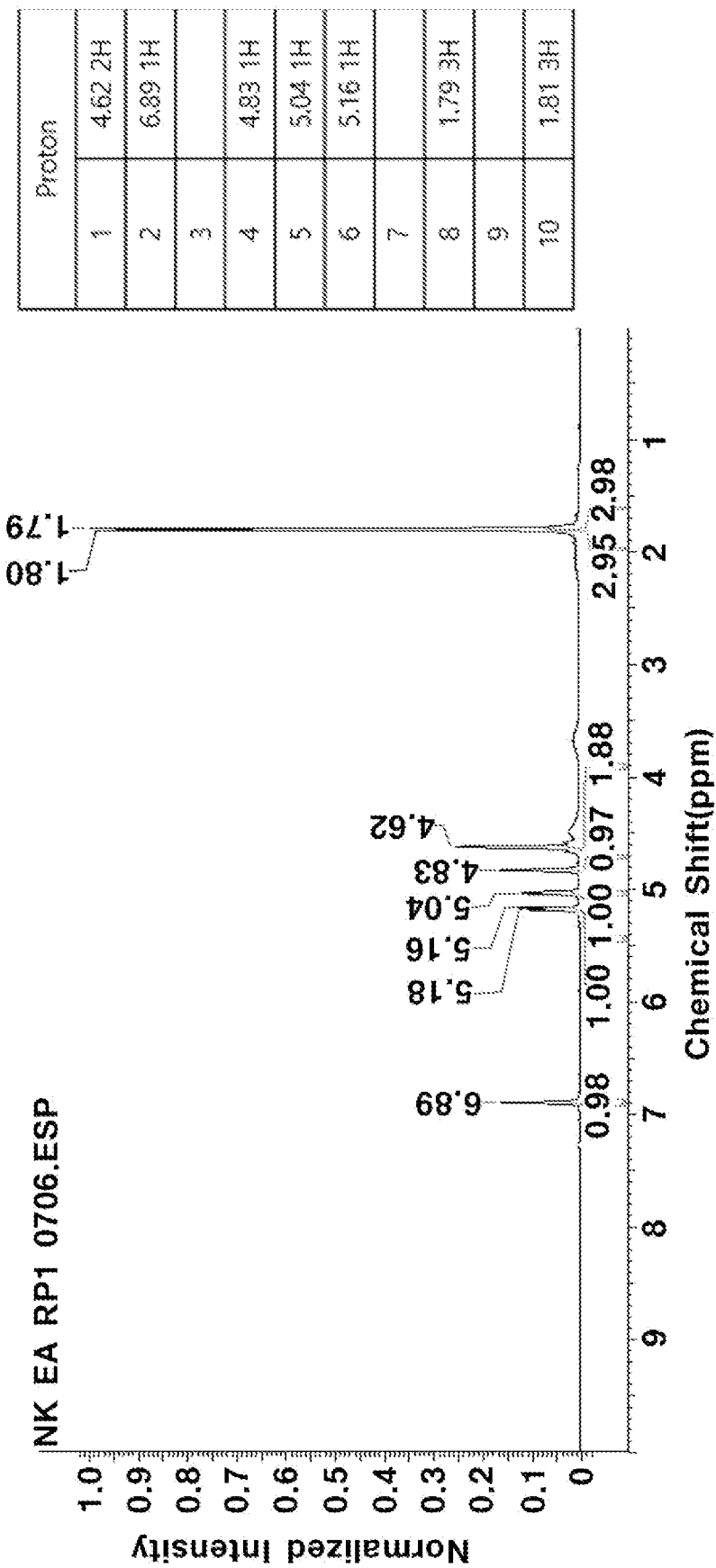
FIG. 3A to 3B show H NMR and c NMR results of compound M2-RP1 in Example 1-4 according to the present invention.
Figure 3B:
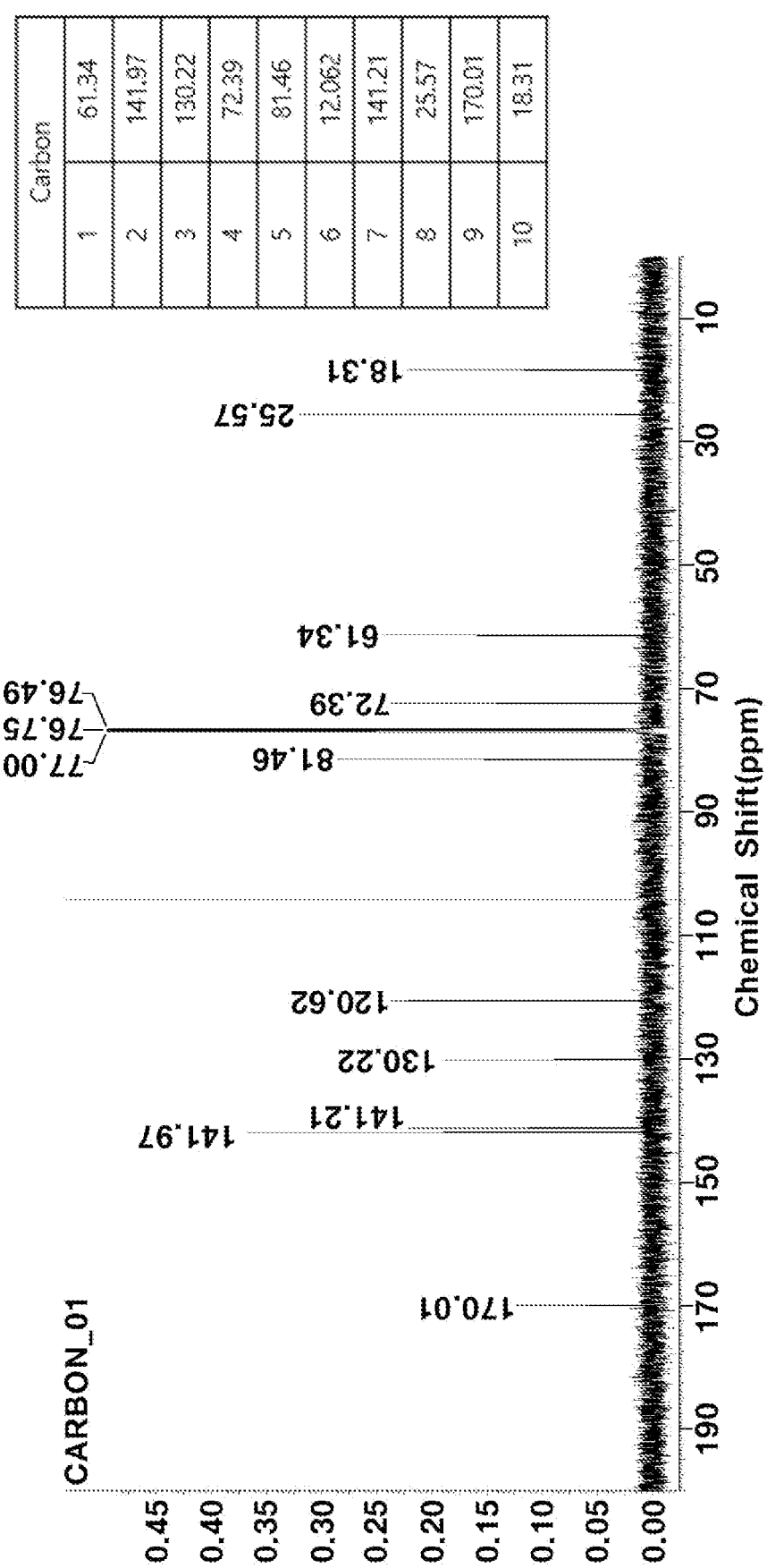

The experimental results are shown in FIG. 3A to 3B.

Accordingly, it was confirmed that the separated component, compound M2-RP1, has the formula $C_{10}H_{14}O_4$ and a molecular weight of 198.22, and the IUPAC name thereof is (Z)-4-Hydroxy-3-(2-hydroxyethylidene)-5-(2-methylprop-1-en-1-yl)dihydrofuran-2(3H)-one.

The compound was identified as cimicifugolide A, and is represented by Chemical Formula 1 below.

[Chemical Formula 1]

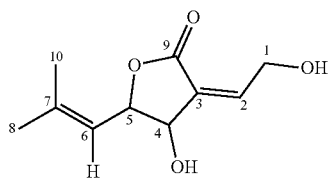

Example 2: Confirmation of Psoriasis Amelioration Effect at Protein Level Through Cell Experiment 2-1. Cells and Cell Culture The cells used in the experiment were HaCaT, and were provided by the Korean Cell Line Bank. The cells were cultured using an incubator at 37° C. and 5% $CO_2$ in Dulbecco's modified Eagle Medium (DMEM) supplemented with 10% (V/V) fetal bovine serum (FBS) and 1% penicillin-streptomycin solution, and were maintained through subculture at intervals of 2-3 days.

2-2. Treatment of Extract Sample

The cells were dispensed at a density of $5 \times 10^5$ cells/well in a 6-well plate and stabilized, after which M2-RP1 dissolved in a serum-free culture medium was added to each well, followed by culture for 24 hours, after which the medium was removed, PBS was added such that the cells were slightly covered therewith, and IL-17a/TNF-α was then added thereto.

2-3. Western Blotting

The cell lysate was lysed with lysis buffer (150 mM NaCl, 50 mM Tris-HCl, 1 mM EDTA, 50 mM NaF, 10 mM $Na_4P_2O_7$, 1% IGEPAL, 2 mM $Na_3VO_4$, 0.25% protease inhibitor cocktail, and 1% phosphatase inhibitor cocktail), followed by protein quantification. 20 μg of the quantified protein was electrophoresed in 10% SDS-PAGE and then transferred to a nitrocellulose membrane for 2 hours. The membrane was blocked with 5% BSA for 1 hour and then detected using antibodies to P-STAT3, STAT3, P-Akt, Akt, P-GSK3β, GSK3β, P-ERK, ERK, P-TBK1, TBK1, IRF3, and P-IRF3.

Cyclosporine A is widely used as an immunosuppressant drug, and is administered orally or intravenously in order to inhibit psoriasis, Crohn's disease, rheumatoid arthritis, and inflammation due to organ transplantation. This drug was used as a positive control in order to evaluate the anti-inflammatory effect.

Figure 4:
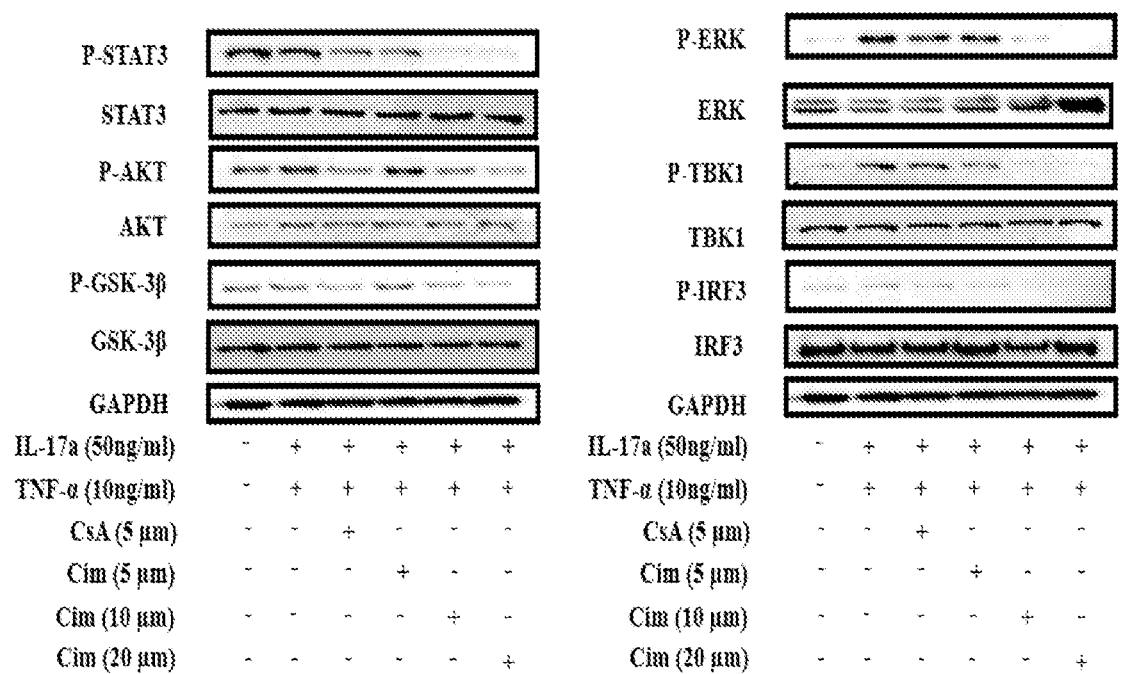
FIG. 4 shows the results of Example 2-3 according to the present invention.
Figure 5A:
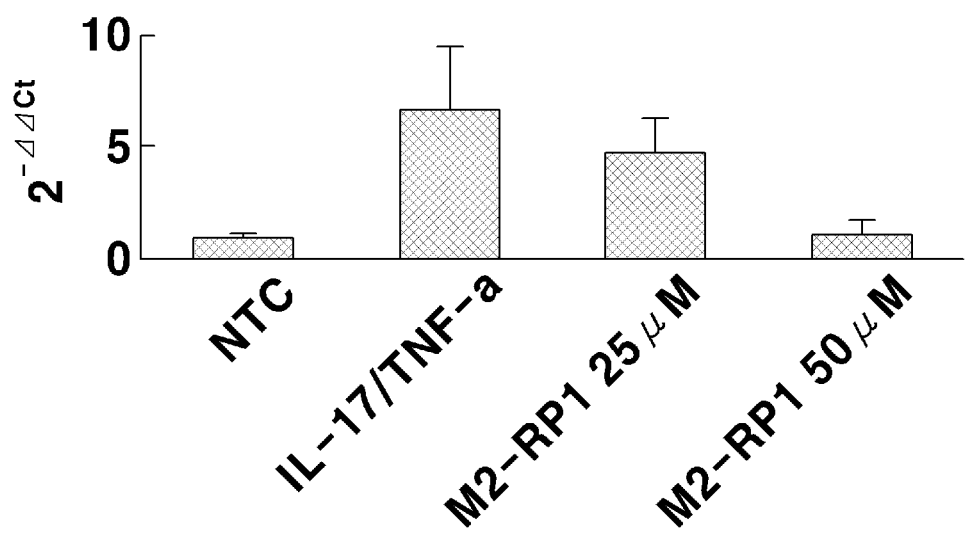
FIGS. 5A to 5F show the results of Example 2-4 according to the present invention.
Figure 5B:
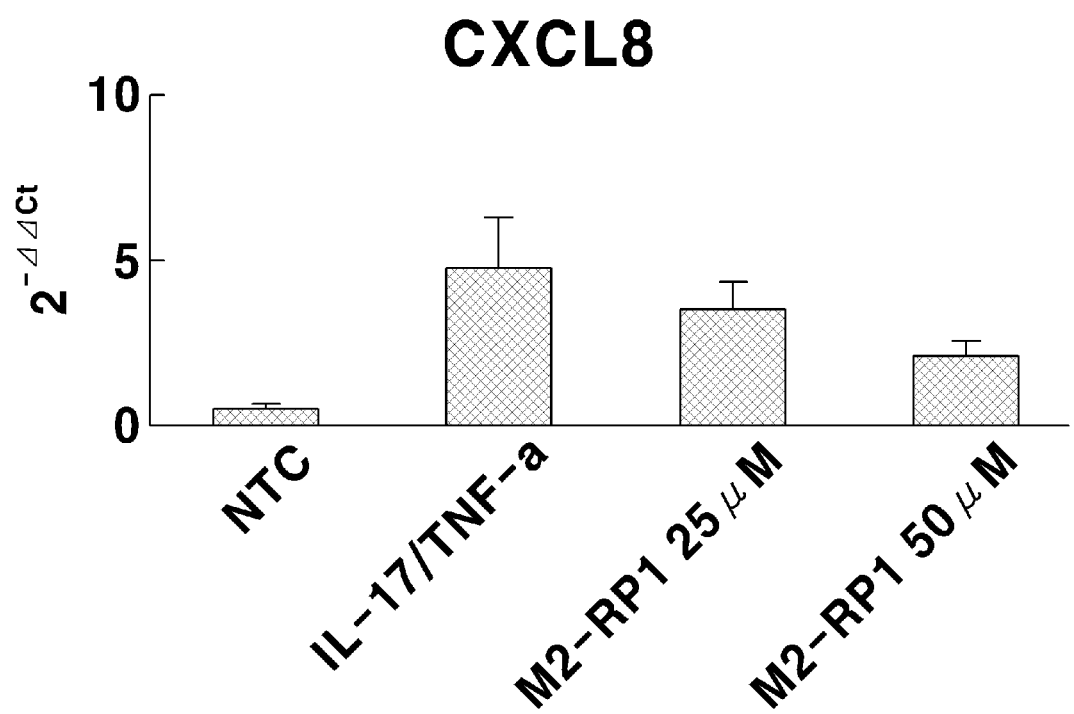
Figure 5C:
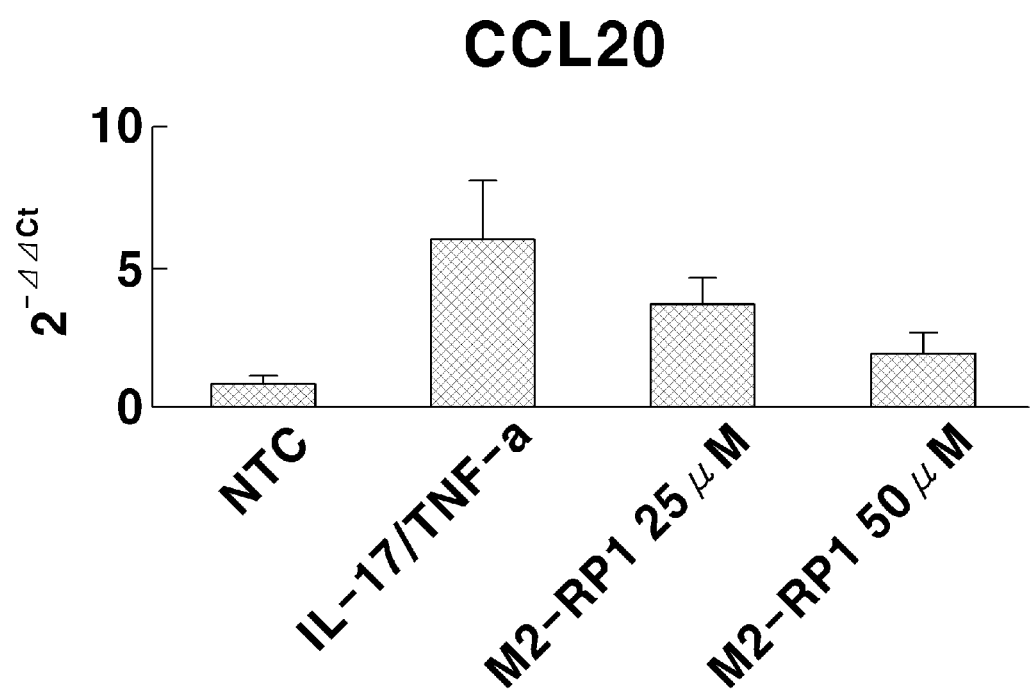
Figure 5D:
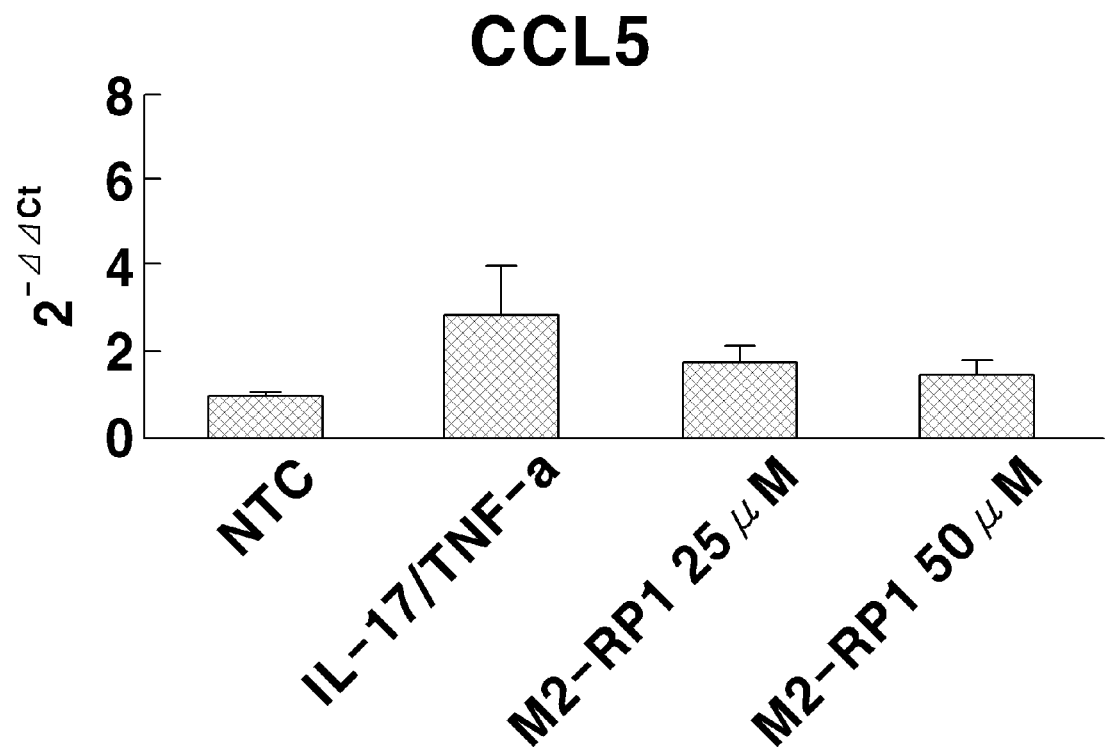
Figure 5E:
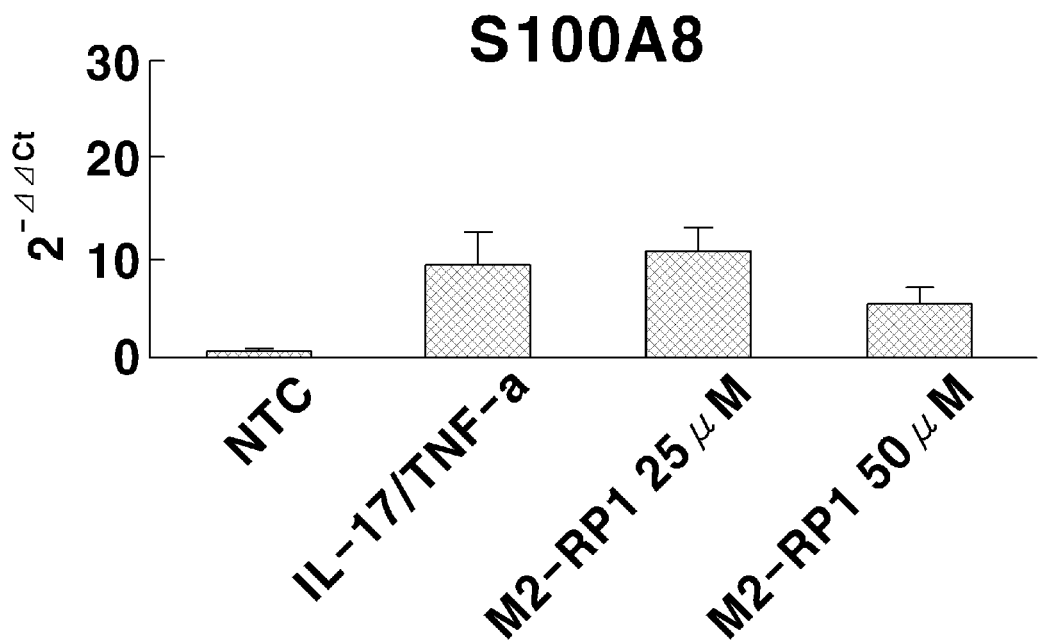
Figure 5F:
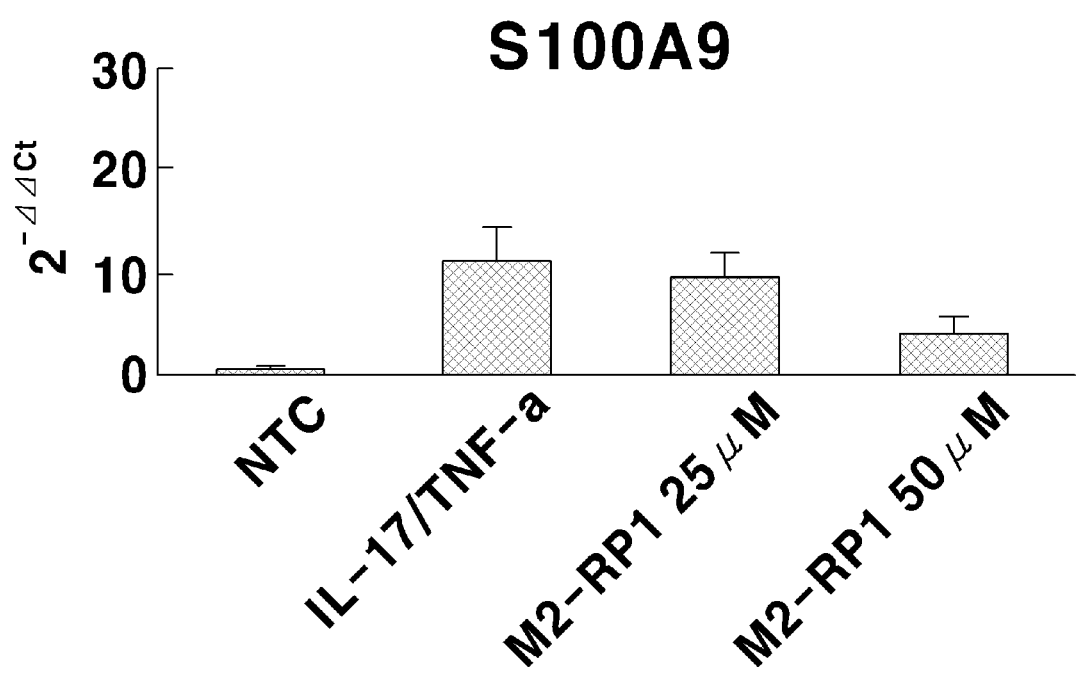

The experimental results are shown in FIG. 4.

2-4. Expression of IL-1B, CXCL-8, CCL_20, CCL-5, S100-A8, and S100-A9 at Cellular RNA Levels HaCaT cells were treated with the extract and IL-17a/TNF-α and then cultured for 24 hours, total RNA was isolated therefrom, and the concentrations of IL-1β, CCL20, and CXCL8 were measured using a qRT-PCR machine.

The concentrations of IL-1β, CXCL-8, CCL_20, CCL-5, S100-A8, and S100-A9 were measured.

The experimental results are shown in FIGS. 5A to 5F.

Below is a description of formulation examples of the composition according to the present invention, which are merely set forth to illustrate, rather than to limit, the present invention.

[Formulation Example 1] Preparation of Pill 30 wt % of Example 1, 30 wt % of corn starch, 20 wt % of glycerin, and 20 wt % of sorbitol powder were mixed and made into pills using a pill maker. The final weight of the resulting formulation was 3.5 g.

[Formulation Example 2] Preparation of Tablet 30 wt % of Example 1, 20.5 wt % of lactose, 20 wt % of dextrin, 20 wt % of maltitol powder, and 7 wt % of xylitol powder were mixed, granulated using a fluidized-bed dryer, added with 2.5 wt % of sugar ester, and tableted using a tableting machine. The final weight of the resulting formulation was 2 g.

[Formulation Example 3] Preparation of Granules 30 wt % of Example 1, 5 wt % of xylitol, and 65 wt % of isomalt were mixed, formed into granules using a fluidized-bed granulator, and the granules were then encapsulated. The final weight of the resulting formulation was 2 g.

[Formulation Example 4] Preparation of Injection Solution

An injection solution was prepared in a typical manner using components in the amounts shown in Table 1 below.

TABLE 1

| Component | Amount |
|---|---|
| Example 1 | 10-50 mg |
| Sterile distilled water for injection | Appropriate amount |
| pH adjuster | Appropriate amount |

[Formulation Example 5] Health Food

A health food was prepared in a typical manner using components in the amounts shown in Table 2 below.

TABLE 2

| Component | Amount |
|---|---|
| Example 1 | 20 mg |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

[Formulation Example 5] Health Drink

A health drink was prepared in a typical manner using components in the amounts shown in Table 3 below.

TABLE 3

| Component | Amount |
|---|---|
| Example 1 | 1000 mg |
| Citric acid | 1000 mg |
| Oligosaccharide | 100 g |
| Taurine | 1 g |
| Purified water | Remainder |

As is apparent from the above description, the composition of the present invention can be used to prevent, alleviate or treat psoriasis. Specifically, the composition is capable of decreasing skin moisture loss due to psoriasis, increasing skin moisture content, and significantly inhibiting changes in skin thickness and the inflammatory response.

The effects of the present invention are not limited to the above-mentioned effects. It should be understood that the effects of the present invention include all effects that can be inferred from the description of the present invention.

Although specific embodiments of the present disclosure have been described with reference to the accompanying drawings, those skilled in the art will appreciate that the present disclosure may be embodied in other specific forms without changing the technical spirit or essential features thereof. Thus, the embodiments described above should be understood to be non-limiting and illustrative in every way.

What is claimed is:

1. A method for ameliorating or treating psoriasis of a subject, wherein the method comprises administering an effective amount of cimicifugolide A of Chemical Formula 1 to the subject in need thereof:

[Chemical Formula 1]

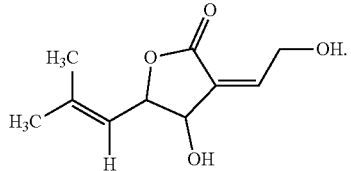

2. The method of claim 1, wherein the cimicifugolide A is administered in a form of a functional health food.

3. The method of claim 1, wherein the cimicifugolide A is administered in a form of a pharmaceutical composition.

4. The method of claim 1, wherein the cimicifugolide A is administered in a form of a functional cosmetic composition.

5. The method of claim 3, wherein the pharmaceutical composition is formulated for skin application.

* * * * *